United States Patent
Ngo et al.

(10) Patent No.: US 7,534,917 B1
(45) Date of Patent: May 19, 2009

(54) METHOD OF PRODUCING DICARBOXYLIC ACIDS

(75) Inventors: Helen Ngo, North Wales, PA (US); Thomas A. Foglia, Lafayette Hill, PA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/786,640

(22) Filed: Apr. 12, 2007

Related U.S. Application Data (60) Provisional application No. 60/795,289, filed on Apr. 27, 2006.

(51) Int. Cl.
C07C 57/02 (2006.01)
C07C 55/00 (2006.01)
(52) U.S. Cl. .................... 562/595; 562/590
(58) Field of Classification Search .............. None
See application file for complete search history.

(56) References Cited

U.S. PATENT DOCUMENTS

| | | | |
|---|---|---|---|
| 5,342,909 A | | 8/1994 | Grubbs et al. |
| 5,728,917 A | * | 3/1998 | Grubbs et al. .......... 585/653 |
| 5,831,108 A | | 11/1998 | Grubbs et al. |
| 6,111,121 A | | 8/2000 | Grubbs et al. |
| 6,211,391 B1 | | 4/2001 | Grubbs et al. |
| 6,515,084 B2 | | 2/2003 | Grubbs et al. |
| 6,806,325 B2 | | 10/2004 | Grubbs et al. |
| 2002/0177710 A1 | * | 11/2002 | Grubbs et al. .......... 546/2 |

OTHER PUBLICATIONS

Ngo et al., JAOCS, vol. 83, No. 7 (2006), 629-634.*
Yi, Zu-Hua et al., "Identification and Production of,Δ9-cis-1, 18-octadecenedioic acid by *Candida tropicalis*," *Applied Microbiology and Biotechnology*, 1989,vol. 30, pp. 327-331.
Warwel, Siegfried. et al., "Polyesters w-Unsaturated Fatty Acid Derivatives," *Macromolecular Chemistry and Physics*, 2001, vol. 202, No. 7, pp. 1114-1121.
Warwel, Siegfried et al., "Copolymerization of Ethylene with w-Unsaturated Fatty Acid Methyl Esters Using a Cationic Palladium Complex," *Macromolecular Chemistry and Physics*,2001, vol. 202, No. 6, pp. 849-855.
Warwel, S. et al., "Polymers and polymer building blocks from Meadowfoam oil," *Industrial Crops and Products*, 2004, vol. 20, pp. 301-309..
Kohashi, Hitoshi et al., "Metathesis od Methyle Oleate with a Homogeneous and a Heterogeneous Catalyst,"*JACOS*, Mar. 1985, vol. 62, No. 3, pp. 549-554.
Holser, Ronald A. et al., "Metathesis of Methyl Soyate With Ruthenium Catalysts," *Fuel*, 2006, vol. 85, pp. 393-395.
Gunatillake, Pathiraja A. et al., "Biodegradable Synthetic Polymers For Tissue Engineering," *European Cells and Materials*, 2003, vol. 5, pp. 1-16.

(Continued)

*Primary Examiner*—Karl J Puttlitz
(74) *Attorney, Agent, or Firm*—John D. Fado; G. Byron Stover

(57) ABSTRACT

A method of producing dicarboxylic acids (e.g., α,ω dicarboxylic acids) by reacting a compound having a terminal COOH (e.g., unsaturated fatty acid such as oleic acid) and containing at least one carbon-carbon double bond with a second generation Grubbs catalyst in the absence of solvent to produce dicarboxylic acids. The method is conducted in an inert atmosphere (e.g., argon, nitrogen). The process also works well with mixed unsaturated fatty acids obtained from soybean, rapeseed, tall, and linseed oils.

33 Claims, 6 Drawing Sheets

1st generation (1)

2nd generation (2)

OTHER PUBLICATIONS

Warwel, Siegfried et al., "Polyesters by Lipase-Catalyzed Polycondensation of Unsaturated And Expoxidized Long-Chain $\alpha$, w-Dicarboxylic Acid Methyl Esters with Diols," *Journal of Polymer Science*, 2001, vol. 39, pp. 1601-1609.

Atomi, Haruyuki et al., "Characterization of a Dicarboxylic Acid-Producing Mutant of the Yeast *Candida tropicalis*," *Journal of Fermentation and Bioengineering*, 1994, vol. 77, No. 2, pp. 205-207.

Trnka, Tina M et al., "The Development of L2X2Ru=CHR Olefin Metathesis Catalysts: An Organometallic Success Story," *Accounts of Chemical Research*, 2001, vol. 34. No. 1, pp. 18-29.

Ngo, Helen et al., "Hybrid Organic—Inorganic Solids for Heterogeneous Asymmetric Catalysis," *Topics in Catalysis*, May 2005, vol. 34, No. 1-4, pp. 85-92.

Ngo, Helen et al., "Metathesis of Unsaturated Fatty Acids: Synthesis of Long-Chain Unsaturated-$\alpha$, $\omega$-Dicarboxylic Acids," *JAOCS*, 2006, vol. 83, No. 7, pp. 629-634.

Scholl, Matthias et al., "Synthesis and Activity of a New Generation of Ruthenium-Based Olefin Metathesis Catalysts Coordinated with 1,3-Dimesityl-4,5-dihydroimidazol-2-ylidene Ligands," *Organic Letters*, 1999, vol. 1, No. 6, pp. 953-956.

Liu, Shuchen et al., "Optimal pH Control strategy for High Level Production of Long-Chain $\alpha$, $\omega$-dicarboxylic acid by *Candida tropicalis*," *Enzyme and Microbial Technology*, 2004, vol. 34, pp. 73-77.

Mao, J. et al., "Diacids Made from Renewable resources and Their Applications in Polymers," *Cognis Corporation, United States, Abstract Biotechnology Posters*, 95th AOCS Meeting and Expo, May 9-12, 2004 Cincinnati, Ohio.

Van Dam, P., et al., "Homogeneous Catalytic Metathesis of Unsaturated Fatty Esters: New Synthetic Method for Preparation of Unsaturated Mono- and Dicarboxylic Acids," *J. of the American Oil Chemists' Society*, vol. 51, 1974, pp. 389-392.

Warwel, S., et al., "Polymers and Surfactants on the Basis of Renewable Resources," *Chemosphere*, vol. 43, 2001, pp. 39-48.

\* cited by examiner

Fig. 1

1st generation (1)  2nd generation (2)

Fig. 2

*Equation 1*

$$CH_3(CH_2)_xCH=CH(CH_2)_yCO_2R \rightleftharpoons CH_3(CH_2)_xCH=CH(CH_2)_yCH_3$$

3a - d

4: x = y = 7

+

$$RO_2C(CH_2)_xCH=CH(CH_2)_yCO_2R$$

5a - d

3a: R = CH$_3$; x = y = 7
3b: R = H;   x = y = 7
3c: R = H;   x = 7, y = 9
3d: R = H;   x = 7, y = 11

5a: R = CH$_3$; x = y = 7
5b: R = H;   x = y = 7
5c: R = H;   x = y = 9
5d: R = H;   x = y = 11

*Equation 2*

$$CH=CH(CH_2)_8CO_2H \longrightarrow HO_2C(CH_2)_8CH=CH(CH_2)_8CO_2H + CH_2=CH_2$$

6                          7

*Equation 3*

$$CH_3(CH_2)_5\underset{OH}{CH}CH_2CH=CH(CH_2)_7CO_2H \rightleftharpoons$$

8

5b
+
$$H_3C(CH_2)_5\underset{OH}{CH}CH_2CH=CHCH_2\underset{OH}{CH}(CH_2)_5CH_3$$

9

Compound 9: R = H
Compound 9a: R = Si(CH$_3$)$_3$

METHOD OF PRODUCING DICARBOXYLIC ACIDS

REFERENCE TO RELATED APPLICATION

This application claims the benefit of U.S. Provisional Application No. 60/795,289, filed 27 Apr. 2006, which is incorporated herein by reference in its entirety.

BACKGROUND OF THE INVENTION

The present invention relates to a method of producing dicarboxylic acids (e.g., α,ω dicarboxylic acids) by reacting a compound having a terminal COOH (e.g., unsaturated fatty acids such as oleic acid) and containing at least one carbon-carbon double bond with a second generation Grubbs catalyst in the absence of solvent to produce dicarboxylic acids. The method is conducted in an inert atmosphere (e.g., argon, nitrogen).

Aliphatic dicarboxylic acids are important intermediates in the synthesis of biodegradable polymers (Gunatillake, P. A., and R. Adhikari, Eur. Cells & Mater., 5: 1-16 (2003)). Short-chain linear-α,ω-dicarboxylic acids such as suberic acid ($C_8$), azelaic acid ($C_9$), or sebacic acid ($C_{10}$), which can be derived from fats and oils by chemical oxidation of unsaturated fatty acids, are particularly important building blocks in the synthesis of commercially important materials such as nylons, cosmetics, plasticizers, lubricants, and greases (Johnson, R. W., Fatty Acids in Industry, Marcel Dekker, New York, 1989; Pattison, E. S., Fatty Acids and their Industrial Applications, Marcel Dekker, New York, p. 301 (1968)). It is known that the chain length of the dicarboxylic acid in polymers not only influences polymer properties but also the degradation rate of the polymers. Accordingly, the availability of a variety of α,ω-dicarboxylic acids of varying chain length could potentially lead to new polymeric materials that have better performance properties and are more biodegradable. Research in producing aliphatic α,ω-dicarboxylic acids of carbon chain-length >10 started in the 1970s. Such long-chain α,ω-dicarboxylic acids were produced by either microbial oxidation or microbial fermentation (Atomi, H., et al., J. Ferment. Bioeng., 77: 205-207 (1994)). In the 1980s, several research groups reported that microorganisms, including *Candida tropicalis* or *Candida cloacae*, could transform n-alkanes and fatty acids to dicarboxylic acids (Liu, S., et al., Enzyme and Microbiol. Technol., 34: 73-77 (2004); Zu Hua, Y., and R. Hans Juergen, Applied Microbiol. and Biotechnol., 30: 327-331 (1989)). Furthermore, α,ω-diacids of $C_{11}$ to $C_{18}$ chain-length are produced in China and unsaturated α,ω-diacids, particularly α,ω-octadecanedioic acid, from vegetable and animal raw materials (Kroha, K., Inform., 15: 568-571 (2004)); using the latter diacid, a series of nylons of both homo- and co-polymers was synthesized (Mao, J., et al., Diacids Made from Renewable Resources and Their Applications in Polymers, Abstract, Biotechnology Posters, 95th AOCS Annual Meeting & Expo, Cincinnati, Ohio (2004)). Although microbial fermentation processes have been used for commercial production of long-chain α,ω-dicarboxylic acids, there are environmental concerns with these processes. Fermentation processes produce aqueous waste containing expired microbial cells, microbial metabolites, and unutilized growth media, which place significant biological demand on water treatment systems. Additionally, the yields of diacids are variable and often poor.

Alternatively, long-chain dicarboxylic acids can be synthesized by chemical approaches. In 1974, there was reported the synthesis of long chain dicarboxylic acids ($C_{18}$-$C_{26}$) by the self-metathesis of monounsaturated carboxylic acid esters in the presence of tungsten hexachloride ($WCl_6$) and tetramethyltin ($Me_4Sn$) co-catalysts in chlorobenzene solution; in this manner, monounsaturated fatty esters such as methyl octadec-9-enoate (methyl oleate, 3a, FIG. 2) were converted to dicarboxylate esters with conversions ranging from 50 to 89% and the diesters could be saponified and acidified to give the long-chain dicarboxylic acids (Van Dam, P. B., et al., J. Am. Oil. Chem. Soc., 51:389-391 (1974)). Subsequently, the co-metathesis of methyl oleate with cis-dimethyl-3-hexendioate was carried out using both homogeneous catalysts ($WCl_6$, $Me_4Sn$) and heterogeneous ($Re_2$—$Al_2O_3$) catalysts (Kohashi, H., et al., J. Am. Oil. Chem. Soc., 62:549-554 (1985)). Although these synthetic approaches gave high selectivity and high conversions, the catalyst systems used suffered from low catalyst turnover numbers.

In the 1990s, it was demonstrated that homogeneous ruthenium-based catalysts were effective in catalyzing olefin metathesis; moreover, these catalysts, in contrast to the tungsten and rhenium catalysts, often tolerate functionally substituted alkenes (Grubbs, R. H., Handbook of Metathesis, Wiley-Vch, Verlag GmbH & Co. KGaA, Weinheim (2003)). Such ruthenium-based catalysts have been used to prepare α,ω-dicarboxylate esters via metathetic routes. For example, a two-step process was reported using Grubbs catalysts to prepare long-chain unsaturated α,ω-dicarboxylate methyl esters (Warwel, S., et al., Polym. Sci. Part A: Polym. Chem., 39: 1601-1609 (2001)). Cross-metathesis of monounsaturated carboxylic acid methyl esters with ethylene in the presence of the first generation catalyst 1 (FIG. 1) in solution initially gave terminally unsaturated monocarboxylate methyl esters. The resulting terminal monounsaturated esters then underwent self-metathesis in the presence of catalyst 1 to give long-chain α,ω-dicarboxylic acid methyl esters with an overall yield between 38-40% (Warwel, S., et al., Polym. Sci. Part A: Polym. Chem., 39: 1601-1609 (2001); Warwel, S., et al., Ind. Crops & Prod., 20: 301-309 (2004); Warwel, S., et al., Macromol. Chem. Phys., 202: 1114-1121 (2001); Warwel, S., et al., Macromol. Chem. Phys., 202: 849-855 (2001); Warwel, S., et al., Chemosphere, 43: 39-48 (2001)). Self-metathesis of methyl oleate in dichloromethane was reported using the second generation Grubbs catalyst 2 (FIG. 1) and gave the long chain α,ω-dicarboxylic methyl ester 5a (FIG. 2, Eq. 1) in ~45% conversion (Dinger, M. B., and J. C. Mol, et al., Adv. Synth. Catal., 344: 671-677 (2002)). The self-metathesis of oleic acid in the presence of $Cl_2(PCy_3)_2Ru$=CH—CH=$CPh_2$ in dichloromethane solution was reported to give 1,18-octadec-9-enedioic acid (5b) and octadec-9-ene (4) in 42% yield (U.S. Pat. No. 5,728,917). However, this process gave low conversion (about 50%) of monounsaturated fatty acids and low yields of dicarboxylic acids. In addition, the reaction was performed in a solvent, dichloromethane, which is an environmental concern.

We have developed an efficient solvent-free self-metathesis process for the conversion of unsaturated hydrocarbons, such as monounsaturated fatty acids, using second generation Grubbs catalysts to afford products such as α,ω-unsaturated dicarboxylic acids and hydrocarbons in very high conversions.

SUMMARY OF THE INVENTION

In accordance with the present invention, there is provided a method of producing dicarboxylic acids by reacting an unsaturated compound having a terminal COOH and containing at least one carbon-carbon double bond with a second generation Grubbs catalyst in the absence of solvent to produce dicarboxylic acids; the method is conducted in an inert atmosphere (e.g., argon, nitrogen).

DETAILED DESCRIPTION OF THE INVENTION

The present invention concerns a method of producing dicarboxylic acids by reacting an unsaturated compound having a terminal COOH and containing at least one carbon-carbon double bond with a second generation Grubbs catalyst in the absence of solvent to produce dicarboxylic acids; the method is conducted in an inert atmosphere (e.g., argon, nitrogen). Preferably, the unsaturated compound should be liquid at 40° C. or above.

The present invention can utilize any carboxylic acid that contains one or more carbon-carbon double bonds that may be located at the terminal or internal positions of the carboxylic acid chain; generally the carbon atom (C) chain-length is C-30 or less. The unsaturated acid may be linear or branched and may contain other functional groups such as hydroxy, epoxy, thiol, and others; generally such compounds can be used in the present invention so long as the carbon-carbon double bond is not sterically encumbered when reacted with the catalysts described herein. Terminal carbon-carbon double bond generally means a carbon-carbon double bond at the end of the hydrocarbon chain opposite the terminal COOH group.

Monounsaturated fatty acids that can be used in the method of the present invention contain an internal carbon-carbon double bond with either a cis (Z) or trans (E) configuration and generally are of chain length with the number of carbon atoms (C) from C-6 to C-30, including lauroleic (C12), myristoleic (C14), palmitioleic (C16), oleic and elaidic (C18), gadoleic (C20), erucic (C22), and others known in the art.

Polyunsaturated fatty acids that can be used in the method of the present invention contain internal carbon-carbon double bonds with either cis (Z) or trans (E) configuration and generally are of chain length with the number of carbon atoms (C) from C-12 to C-30 and the number of double bonds (n) equal to 2 to 6, especially those unsaturated fatty acids that are commonly found in fats and oils such as linoleic and linolenic (alpha or gamma), but also including the less common fatty acids such as arachadonic, docosadienoic acid, eicosatrienoic acid, arachadonic acid, eicosatetraenoic acid, docosatetraenoic acid, decosapentaenoic acid, eicosapentaenoic acid, docosahexaenoic acid, tetracosahexaenoic acid, and others known in the art. The fatty acids, typically are C-12 to C-24 in chain length, and may be branched chain or contain additional functional groups such as hydroxyl, carboxylate, epoxy, thiol, keto, and others known in the art; such fatty acids are known in the art.

The present invention can also utilize terminally unsaturated fatty acids with carbon atom (C) chain-length of generally from C-6 to C-30, such as 10-undecenoic acid, 9-decenoic acid, and others known in the art.

Preferably, the unsaturated compounds utilized in the present invention are oleic acid, erucic acid, or ricinoleic acid. The unsaturated compound may be found in soybean acid (acids obtained by hydrolysis of soybean oil) or acids obtained from other oilseeds such as rapeseed, sunflower, safflower, or linseed, and other sources of fatty acids such as tall oil (a byproduct of the Kraft process of wood pulp manufacture and contains fatty acids such as palmitic acid, oleic acid and linoleic acid).

Preferably the dicarboxylic acids produced are 1,18-octadec-9-enedioic acid, 1,26-hexacos-13-enedioic acid, or 1,20-eicos-10-enedioic acid.

The purity of the starting unsaturated fatty acids may range from about 60 to about 99% (e.g., 60-99%), preferably about 70 to about 99% (e.g., 70-99%), more preferably about 80 to about 99% (e.g., 80-99%), and most preferably about 90 to about 99% (e.g., 90-99%).

The second generation Grubbs catalysts utilized in the present invention, preferably ruthenium-based, are representative of the most common catalysts currently used in conventional metathesis chemistry and one skilled in the art would readily understand the term "second generation Grubbs catalysts" and "ruthenium-based second generation Grubbs catalysts." The second generation Grubbs catalysts have been described in numerous publications, including the following U.S. Pat. Nos. 6,806,325; 6,515,084; 6,211,391; 6,111,121; 5,831,108.

Generally, the second generation Grubbs catalysts are ruthenium and osmium alkylidene complexes of the general formula where $R^1$ is hydrogen and R is selected from the specific group described below. Generally X and $X^1$ can be any anionic ligand and L and $L^1$ can be any neutral electron donor. R may be hydrogen, substituted or unsubstituted alkyl, or substituted or unsubstituted aryl. The ruthenium and osmium carbene complexes are stable in the presence of a variety of functional groups. A consequence of this is that the alkyl and aryl R groups may contain a variety of functional groups including alcohol, thiol, ketone, aldehyde, ester, ether, amine, imine, amide, nitro, carboxylic acid, disulfide, carbonate, isocyanate, carbodiimide, carboalkoxy, and halogen groups.

Preferably R is hydrogen, $C_{1-20}$ alkyl, or aryl. The $C_{1-20}$ alkyl may optionally be substituted with one or more aryl, halide, hydroxy, $C_{1-20}$ alkoxy, or $C_{2-20}$ alkoxycarbonyl groups. The aryl may optionally be substituted with one or more $C_{1-20}$ alkyl, aryl, hydroxyl, $C_{1-5}$ alkoxy, amino, nitro, or halide groups. More preferably, R is hydrogen, $C_{1-4}$ alkyl, phenyl, $C_{1-4}$ alkyl substituted with one or more groups selected from the group consisting of halide, hydroxy, and $C_{2-5}$ alkoxycarbonyl, or phenyl substituted with one or more groups selected from the group consisting of $C_{1-5}$, $C_{1-5}$ alkoxy, amino, nitro, and halide.

More preferably R may be hydrogen, methyl, ethyl, n-butyl, iso-propyl, —$CH_2Cl$, —$CH_2CH_2CH_2OH$, —$CH_2OAc$, phenyl. The phenyl may optionally be substituted with a chloride, bromide, iodide, fluoride, —$NO_2$, —$NMe_2$, methoxy, or methyl group. In a more preferred embodiment, the phenyl is para-substituted. More preferably R is phenyl.

Preferred complexes include where R is cyclohexyl, cyclopentyl, iso-propyl, or phenyl.

The most preferred complex is

Specific ruthenium-based second generation Grubbs catalysts that can be used in the present invention include 1,3-bis-(2,4,6-trimethylphenyl)-2-(imidazolidinylidene)(dichlorophenylmethylene)(tricyclohexylphosphine)ruthenium and (1,3-Bis-(2,4,6-trimethylphenyl)-2-imidazolidinylidene) dichloro(o-isopropoxyphenylmethylene)ruthenium.

Generally the reaction proceeds under conditions (e.g., time, temperature) effective to produce dicarboxylic acids. The reaction time can vary from about several minutes to about several days, but generally is from about 0.5 hour to about three days (e.g., 0.5 hour-3 days), preferably about 0.5 to about 24 hours (e.g., 0.5-24 hours), more preferably about 0.5 to about 12 hours (e.g., 0.5-12 hours), and most preferably about 0.5 to about 2 hours (e.g., 0.5-2 hours). The reaction temperature is generally from about 20° to about 100° C. (e.g., 200 to 100° C.), preferably from about 40° to about 60° C. (e.g., 400 to 60° C.), more preferably from about 40° to about 55° C. (e.g., 40° to 55° C.), more preferably from about 45° to about 55° C. (e.g., 45° to 55° C.), more preferably from about 45° to about 50° C. (e.g., 45° to 50° C.), and most preferably about 45° C. (e.g., 45° C.). The pH is generally between about pH 4 to about pH 8 (e.g., pH 4-8), preferably about pH 6 to about pH 7 (e.g., pH 6-7). Catalyst loadings are generally from about 0.001 mol % to about 5 mol % of reactants (e.g., 0.001-5 mol %), preferably about 0.001 mol % to about 0.1 mol % of reactants (e.g., 0.001-0.1 mol %). Catalyst turnover numbers (TON) are generally in the range of about 800 to about 20,000 (e.g., 800-20,000), preferably about 5,000 to about 20,000 (e.g., 5,000-20,000), preferably about 10,000 to about 20,000 (e.g., 10,000-20,000), more preferably about 12,000 to about 20,000 (e.g., 12,000-20,000), and most preferably about 15,000 to about 20,000 (e.g., 15,000-20,000). The yields are generally about 40% to about 90% (e.g., 40-90%), preferably about 50% to about 90% (e.g., 50-90%), preferably about 55% to about 90% (e.g., 55-90%), preferably about 60% to about 90% (e.g., 60-90%), preferably about 65% to about 90% (e.g., 65-90%), more preferably about 70% to about 90% (e.g., 70-90%), most preferably about 75% to about 90% (e.g., 75-90%). Molar conversions are generally about 40% to about 90% (e.g., 40-90%), preferably about 50% to about 90% (e.g., 50-90%), preferably about 55% to about 90% (e.g., 55-90%), preferably about 60% to about 90% (e.g., 60-90%), preferably about 65% to about 90% (e.g., 65-90%), preferably about 70% to about 90% (e.g., 70-90%), more preferably about 75% to about 90% (e.g., 75-90%), most preferably about 80% to about 90% (e.g., 79-90% or 80-90%).

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Example 1

Materials and Methods

Oleic acid (99%) and 11-eicosenoic acid (99%) were from NU Chek Prep, Elysian, Minn. Oleic acid (90%), erucic acid (90%), undecenoic acid (98%), and the Grubbs catalysts (1 and 2) were purchased from Aldrich Chemical (Milwaukee, Wis.). All other reagents used were of the highest purity obtainable from commercial suppliers.

$^1H$ and $^{13}C$ NMR spectra were collected at room temperature in $CD_3OD$ either on a Varian Gemini 200-MHz or Varian Inova 400-MHz (Palo Alto, Calif.) spectrometer. Operating parameters for $^1H$ NMR were as follows: cycle time (d1)=1.0 s; acquisition time (at)=3.744 s; transmitter power (tpwr)=57 Hz; pulse width (pw)=90°. Operating parameters for $^{13}C$ NMR were as follows: cycle time (d1)=2.0 s; acquisition time (at)=2.399 s; transmitter power (tpwr)=52 Hz; pulse width (pw)=45°. GC/MS characterization of products was carried out with a Hewlett Packard (Agilent, Wilmington Del.) HP 5890 instrument with a capillary inlet (splitless mode) and an HP Model 5972 mass detector set to scan from 40 to 550 m/z at a rate of 1.5 scans/s. The capillary column used was a HP DB-5 column (30 m×0.25 mm×0.25 μm) with carrier gas (He) set at a linear velocity of 22 cm/sec at 100° C. The injector and detector transfer line temperatures were set at 250° and 280° C., respectively. The oven temperature profile was as follows: initial temperature 100° C.; ramp at 10° C./min to 250° C.; hold for 5 min.; ramp at 10° C./min. to 300° C. hold for 5 min.

Synthesis of 1,18-octadec-9-enedioic acid (5b): Oleic acid ((3b), 89 g (90%, 0.315 mol) was transferred into a 250 mL 3-neck round bottom flask via syringe and out-gassed with nitrogen gas for 0.5 h. 1,3-Bis-(2,4,6-trimethylphenyl)-2-(imidazolidinylidene)(dichlorophenylmethylene)(tricyclohexylphosphine)ruthenium (2, 267 mg, 0.315 mmol), a second generation Grubbs catalyst, was then added; no solvent was utilized. The reaction mixture was stirred with a mechanical stirrer and heated at 45° C. and after about 5 minutes a white precipitate formed. After 24 h reaction, about 10 mg of crude product was removed from the reaction mixture and transferred to a 2 mL dram vial. The crude diacid product (5b, eq. 1) was added to 1 mL of methanol and two drops of conc. sulfuric acid were added. The resulting mixture was heated at 80° C. for 0.5 h (Christie, W. W., Lipid analysis:

Isolation, Separation, Identification, and Structural Analysis of Lipids, Oxford, N.Y. Pergamon Press (1982)). The reaction mixture was then quenched with 2 mL of 1M $Na_2CO_3$, extracted with diethyl ether (3×2 mL) and the combined ether layers washed with water (3×2 mL). The organic layer was dried with $MgSO_4$, filtered, solvent removed under reduced pressure, and the methylated diacid 5b characterized by GC/MS: (retention time=14.2 min) and gave an $[M]^+$ of m/z 340 (calc., $[M]^+$ for 5b is m/z=340.26).

The remainder of the crude product was quenched with ethyl vinyl ether (20 mL) and excess ether was removed under reduced pressure. The residue was recrystallized from a mixture of hexane (300 mL) and ethyl acetate (50 mL) twice to give pure 1,18-octadec-9-enedioic acid (5b, eq. 1) as a white solid, m. p., 97.5-98.5° C. (lit. m. p., 88° C. (Van Dam, P. B., et al., J. Am. Oil. Chem. Soc., 51: 389-391 (1974)). Isolated yield: 35 g (71%). $^1$H NMR of 1,18-octadec-9-enedioic acid ($CD_3OD$, 400 MHz): δ 5.39 (m, —CH═CH—, 2H), 2.28 (t, J=7.2 Hz & 7.6 Hz, —$CH_2CO_2H$, 4H), 1.98 (m, 4H), 1.60 (m, 4H), 1.32 (m, 16H). $^{13}$C NMR ($CD_3OD$, 100 MHz): δ 177.8 (s, $CO_2H$), 131.6 (s, CH═CH), 35.1 (s), 33.7 (s), 30.8 (s), 30.4 (s), 30.3 (s), 30.2 (s), 26.2 (s).

Synthesis of 1,22-docos-11-enedioic acid (5c): 1,22-Docos-11-enedioic acid (5c) was synthesized from 3c as described above in the self-metathesis of oleic acid (3b). Pure 5c was obtained by recrystallization from a mixture of hexane (100 mL) and ethyl acetate (10 mL) to give 5c in 74% yield (m.p.=104-106.5° C.). The methyl ester of diacid 5c was analyzed by GC/MS: (retention time t=24 min) and had an $[M]^+$ of m/z 396 (calc., $[M]^+$ for 5c is m/z=396.60). $^1$H NMR ($CD_3OD$, 400 MHz): δ 5.4 (m, —CH═CH—, 2H), 2.28 (t, J=7.6 Hz & 7.2 Hz, —$CH_2CO_2H$, 4H), 1.99 (m, 4H), 1.58 (m, 4H), 1.31 (m, 24H). $^{13}$C NMR ($CD_3OD$, 100 MHz): δ 177.9 (s, $CO_2H$), 131.7 (s, CH═CH), 35.2 (s, $CH_2CO_2H$), 33.7 (s), 30.9 (s), 30.7 (s), 30.6 (s), 30.5 (s), 30.4 (s), 30.3 (s), 26.2 (s).

Synthesis of 1,26-hexacos-13-enedioic acid (5d): Diacid 5d was synthesized from 3d as above. The pure diacid was obtained by recrystallization from acetone in a yield of 70%, m.p.=105-107.5° C. (lit. m.p.=96° C. (Van Dam, P. B., et al., J. Am. Oil. Chem. Soc., 51: 389-391 (1974)). $^1$H NMR ($CD_3OD$, 200 MHz): δ 5.4 (m, CH═CH, 2H), 2.28 (t, J=7.4 Hz & 7.4 Hz, $CH_2CO_2H$, 4H), 1.97 (m, $CH_2CH$═CH, 4H), 1.6 (m, 4H), 1.30 (m, 32H). $^{13}$C NMR ($CD_3OD$, 50 MHz): δ 177.9 (s, —$CO_2H$), 131.7 (s, —CH═CH—), 35.2 (s), 33.7 (s), 30.9 (s), 30.8 (s), 30.78 (s), 30.7 (s), 30.6 (s), 30.4 (s), 30.3 (s), 26.3 (s). The methyl ester of diacid 5d was analyzed by GC/MS (retention time t=28.2 min) and had an $[M]^+$ of m/z 452 (calc., $[M]^+$ m/z 452.38).

Synthesis of 1,20-eicos-1,0-enedioic acid (7): Similar to oleic acid above, undecenoic acid (6, 10 g (98%), 0.054 mol) underwent self-metathesis in the presence of 46 mg (0.054 mmol) of catalyst 2. The reaction flask was attached to a mineral oil bubbler, which allowed the gaseous ethylene coproduct to escape. The mixture was stirred with a mechanical stirrer and heated at 45° C. and after about 5 min. reaction a white precipitate was observed. After 72 h reaction a small amount of the crude product was removed from the reaction mixture and methylated as above for GC/MS analysis.

The remainder of the reaction mixture was quenched with ethyl vinyl ether (about 20 mL) and unreacted ether removed under reduced pressure. The residue was recrystallized twice from about 100 mL of acetone to give pure 1,20-eicos-1,0-enedioic acid as a white solid with m. p.=110-110.5° C. (lit. m. p. 108° C. (Van Dam, P. B., et al., J. Am. Oil. Chem. Soc., 51: 389-391 (1974)). The isolated yield was 7.5 g (82%). The methyl ester of diacid 7 was analyzed by GC/MS (retention time t=23.9 min) and had an $[M]^+$ of m/z 368 (calc., $[M]^+$ m/z for 368.30). $^1$H NMR ($CD_3OD$, 400 MHz): δ 5.39 (m, —CH═CH—, 2H), 2.28 (t, J=7.2 Hz & 7.6 Hz, —$CH_2CO_2H$, 4H), 1.97 (m, 4H), 1.58 (m, 4H), 1.31 (m, 20H). $^{13}$C NMR ($CD_3OD$, 100 MHz): δ 177.8 (s, —$CO_2H$), 131.7 (s, —CH═CH—), 35.1 (s), 33.7 (s), 30.9 (s), 30.6 (s), 30.4 (s), 30.2 (s), 30.2 (s), 26.2 (s).

Synthesis of 7,12-dihydroxyoctadec-9-ene (9): Similar to oleic acid above, ricinoleic acid (8, 400 mg 1.34 mmol) was mixed with 2 (11 mg, 0.013 mmol) in a 50 mL Schlenck tube under nitrogen gas flow and the mixture was heated at 50° C. After about 0.5 h, a small amount of white precipitate was observed in the reaction flask. After 3 days of stirring at 50° C., the reaction mixture was quenched with 2 mL of ethyl vinyl ether and the volatile components removed under reduced pressure. The crude product contains the diol 9, ricinoleic acid, and diacid 5b was methylated using the procedure described above. The methylated product (116 mg) was reacted with 400 μL of N,O-bis(trimethylsilyl)trifluoroacetamide and 120 μL of pyridine at room temperature for 1 h (Christie, W. W., Lipid analysis: Isolation, Separation, Identification, and Structural Analysis of Lipids, Oxford, N.Y. Pergamon Press (1982)). The silylated product was purified by passage through a silica gel column (about 20 g, I.D. X Length (0.5"×10")) using hexane:ethyl acetate (9:1 v/v) as eluant to give 34.5 mg of 7,12-bis(trimethylsiloxy)octadec-9-ene (9a) as yellow oil, 28.9 mg of the silylated methyl ester of 8 and 35.3 mg of the methyl ester of 5b. $^1$H NMR of 9a ($CDCl_3$, 200 MHz): δ 5.43 (m, —$CH_2CH$═CH, 2H), 3.6 (m, —CHOSi($CH_3$)$_3$, 2H), 2.14 (m, —$CH_2CH$═CH, 4H), 1.26 (m, 20H), 0.878 (m, 6H), 0.085 (s, —OSi($CH_3$)$_3$, 18H). $^{13}$C NMR of 9a ($CDCl_3$, 50 MHz): δ 129.1 (s, —CH═CH—), 72.7 (s, —CHOSi($CH_3$)$_3$), 41.2 (s), 37.1 (s), 31.9 (s), 29.4 (s), 25.7 (s), 22.6 (s), 14.1 (s, —$CH_3$), 0.414 (s, —OSi($CH_3$)$_3$). GC/MS of 9a (retention time t=15.8 min) gave an $[M]^+$ atm/z=427 (calc., $[M]^+$ for 9a is m/z=428.84). Yield of 9 was 40%.

Figure 1:
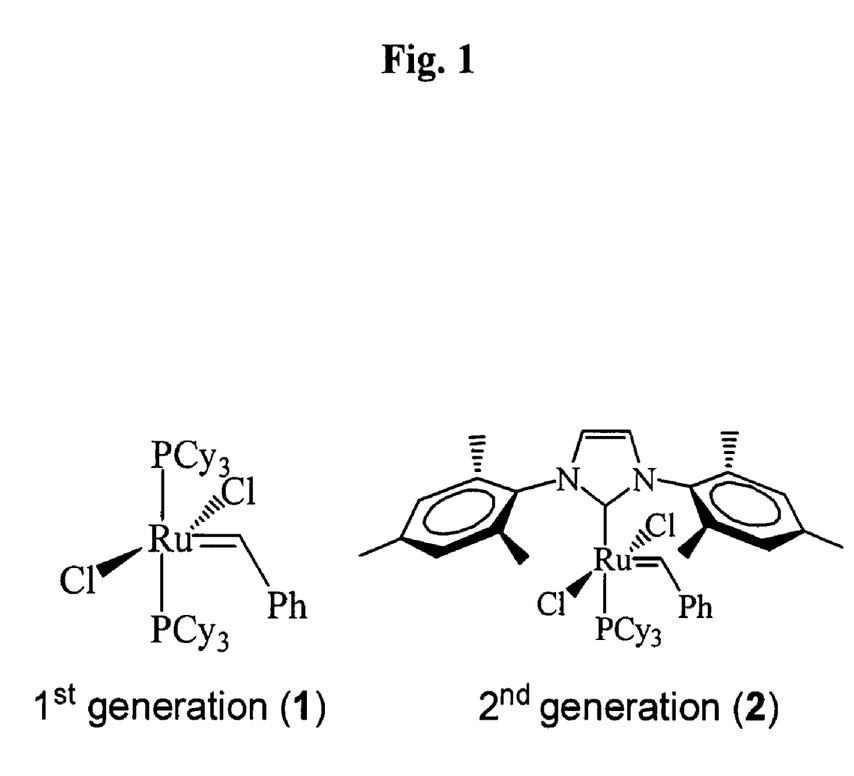
FIG. 1 shows examples of first and second generation Grubbs catalysts.
Figure 2:
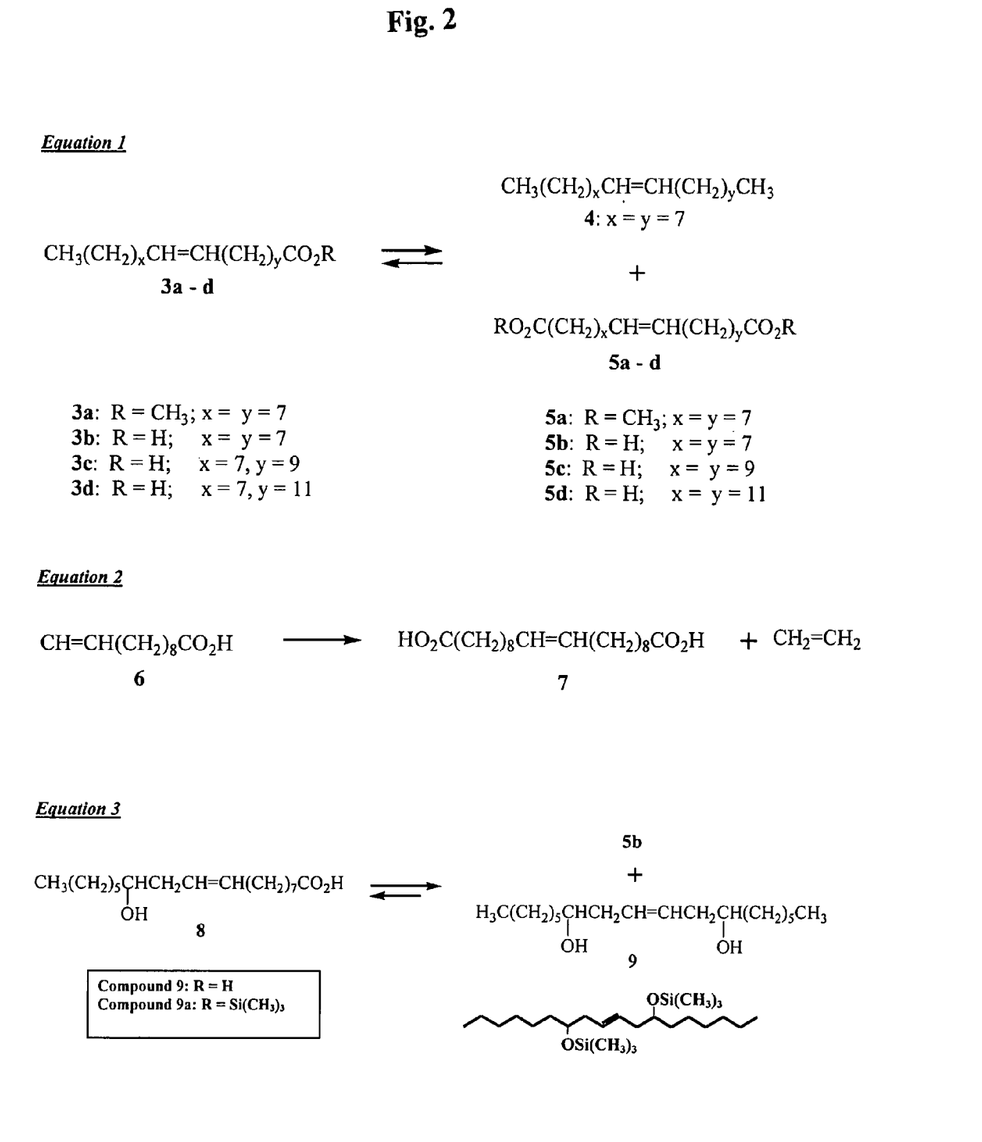
FIG. 2 shows the self-metathesis of various unsaturated fatty acids in the presence of ruthenium catalyst 2.

Results and Discussion: The solvent-free self-metathesis of oleic acid was carried out under a nitrogen atmosphere with 0.1 mol % of second generation Grubbs catalyst 2 (FIG. 1). At a temperature of 45° C., a white precipitate started to form after about five minutes of reaction. Prolonged stirring of this mixture (48 h) led to the formation of 1,18-octadec-9-enedioic acid (5b) and octadec-9-ene (4), two potentially important oleochemical intermediates in 79% conversion (FIG. 2, Eq. 1). After quenching the reaction, the mixture was crystallized from hexane/ethyl acetate to give analytically pure 5b in 71% isolated yield (Table 1, entry 2). Octadec-9-ene (4) was purified by silica-gel column chromatography of the resulting crystallization filtrate (after removal of solvent) using hexane as the eluant. All long-chain, unsaturated α,ω-dicarboxylic acids and coproduct alkenes reported in the examples were characterized by $^1$H and $^{13}$C NMR spectroscopy and GC/MS. Oleic acid of varying purity (90% and 99%) was used and it was found that the self-metathesis reaction surprisingly works equally well for both oleic acids, indicating the tolerance of 2 to the impurities in the starting oleic acid, which were primarily saturated fatty acids. The level of conversion achieved here was surprisingly higher than that previously obtained for ruthenium-catalyzed self-metathesis of fatty acids (Dinger, M. B., and J. C. Mol, et al., Adv. Synth. Catal., 344: 671-677 (2002)). For comparison, we carried out a control experiment with methyl oleate under similar conditions (Entry 1 in Table 1); the self-metathesis of methyl oleate (3a) resulted in an equilibrium distribution of products (50% conversion of 3a) and an isolated yield (39%) of 1,18-dimethyl-9-octadecenedioate (5a) as obtained by silica-gel column chromatography of the crude reaction mixture. The surprisingly significant difference in conversion between oleic acid and methyl oleate was a result of the surprisingly low solubility of diacid 5b in the oleic acid and octadec-9-ene reaction mixture. As self-metathesis of 3b proceeded, diacid 5b precipitated out of the solution and the equilibrium was shifted to the right (FIG. 2, Eq. 1); without being bound by theory, we believe this was because of Le Chatelier's Principle.

Surprisingly, as shown in Table 1, the solvent-free self-metathesis reaction was general and other fatty acids were self-metathesized using catalyst 2 under similar conditions to give the unsaturated dicarboxylic acids and hydrocarbons listed in Table 1 in comparatively high conversions. In addition to oleic acid, the self-metathesis of 11-eicosenoic (3c) and erucic (3d) acids were also investigated and surprisingly in both cases a high conversion to diacids 5c and 5d (FIG. 2, Eq. 1) was obtained. The self-metathesis of undecenoic acid (6) surprisingly resulted in high yields of diacid 7 (FIG. 2, Eq. 2); without being bound by theory, we believe this was because the co-product ethylene readily escaped from the reaction mixture, which further shifted the reaction equilibrium to the right. Surprisingly, in this instance, a conversion of 87% was obtained and analytically pure 1,20-eicos-10-enedioic acid was obtained in 82% isolated yield.

Surprisingly, the solvent-free self-metathesis reaction also worked well for fatty acids containing additional functional groups. For example, surprisingly ricinoleic acid, which has a hydroxyl group on the $12^{th}$ position of the alkyl chain, underwent self-metathesis to afford 1,18-octadec-9-enedioic acid and 7,12-dihydroxyoctadec-9-ene with high selectivity and conversion up to 63% (FIG. 2, Eq. 3).

Surprisingly, it also was found that the self-metathesis of monounsaturated fatty acids worked well at low catalyst loading (Table 2). For example, self-metathesis of undecenoic acid at a catalyst loading of 0.01 mol % surprisingly gave 1,20-eicos-10-enedioic acid with high selectivity and conversion up to 64%. Self-metathesis of oleic acid with 0.005 mol % catalyst loading surprisingly gave 1,18-octadec-9-enedioic acid and octadec-9-ene with high selectivity and 54% conversion. Surprisingly, a turnover number as high as 10,800 was obtained under these non-optimized conditions. Since the catalyst used is expensive, it is important that the reactions work well using small amounts of catalysts and that high catalyst turnover numbers (TON=(% conversion/mol % catalyst loading) be obtained at low catalyst loadings. The higher the catalyst TON the more efficient the process and the more product can be obtained for unit of catalyst used.

Figure 3:
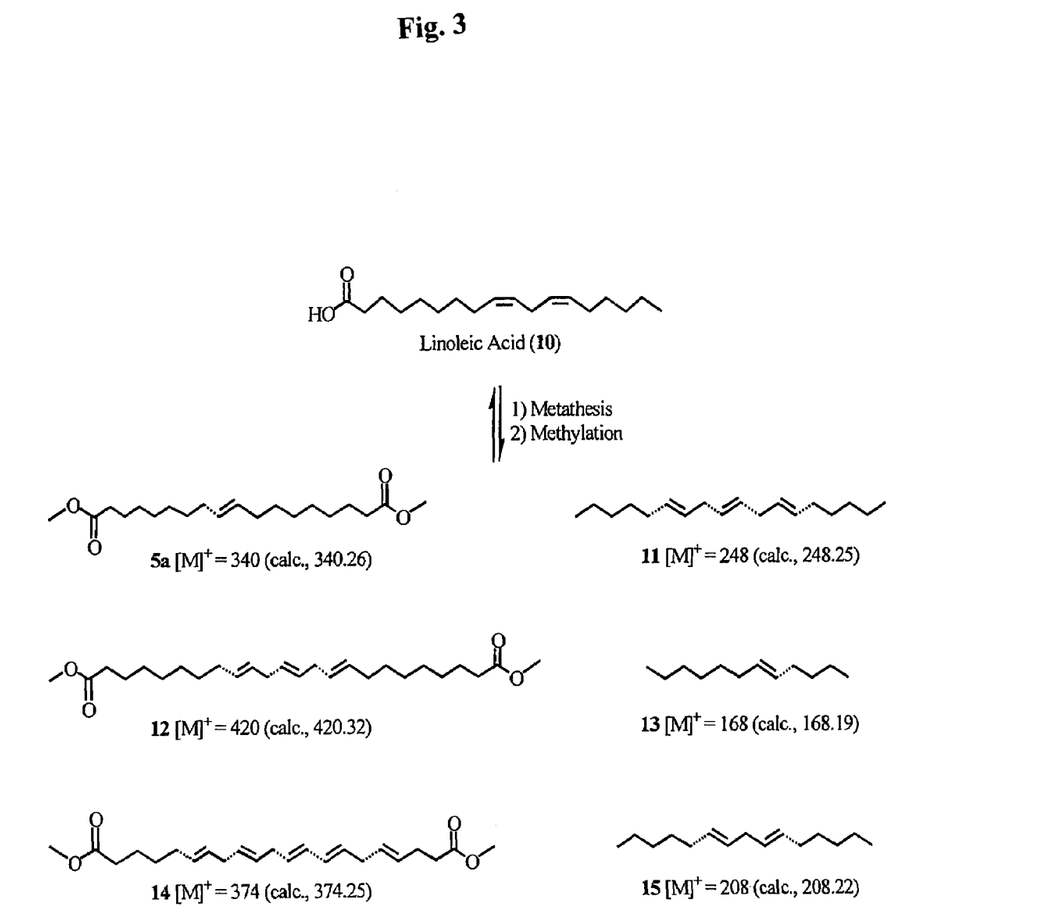
FIG. 3 shows self-metathesis of a polyunsaturated fatty acid such as linoleic acid (10) in the presence of ruthenium catalyst 2 to yield a complex product mixture of unsaturated dicarboxylic acids.

Self-metathesis of linoleic acid (10) in the presence of ruthenium catalyst 2 gave a more complex product mixture (FIG. 3) since both double bonds in linoleic acid were subject to self-metathesis. For example, self-metathesis of both of the 9,10 double bond between two linoleic acid molecules yields $C_{18}$-diacid 5b and $C_{18}$-triene 11 (FIG. 3) whereas metathesis between both of the 12,13 double bonds gives $C_{24}$-diacid 12 and the $C_{12}$-monoene 13 (FIG. 3). Alternatively, self-metathesis can occur between the 9,10 double bonds of one linoleic acid molecule and the 12,13 double bond of a second linoleic acid molecule. The complexity of this reaction was further compounded, since each of the newly formed alkenes and unsaturated acids can in turn undergo cross metathesis to produce compounds 14 and 15 (FIG. 3) so that a very complex product mixture was obtained. Although we have not determined all the hydrocarbon and carboxylic acid products present in this mixture, we were able to identify the compounds shown in FIG. 3 by GC/MS techniques and estimate a conversion of 56% based on the amount of unreacted linoleic acid. Thus the process also surprisingly worked with starting fatty acids that contained two C=C in the alkyl chain and the mixed diacid products were isolated from the reaction mixture by chromatographic methods such as column chromatography.

Thus we have surprisingly developed a facile route to the synthesis of long chain symmetrically unsaturated α,ω-dicarboxylic acids and terminally unsaturated substituted fatty acids using a second generation Grubbs olefin metathesis catalyst. Surprisingly, this solvent-free metathesis process worked well with monounsaturated fatty acids of varying purity (from 90% to 99%) and also was tolerant of the hydroxy functional group present in a monounsaturated fatty acid. Surprisingly high conversions were obtained for all fatty acids when the reactions were performed under solvent-free conditions. Surprisingly, catalyst loadings as low as 0.005 mol % were found to be effective in catalyzing the self-metathesis of fatty acids and proceeded with high selectivity and high catalyst turnover numbers (up to 10,800). This suggests a potentially practical approach for large-scale production of useful unsaturated α,ω-dicarboxylic acids and long-chain unsaturated hydrocarbons by solvent-less ruthenium-catalyzed self-metathesis of readily available unsaturated fatty acids.

Without being bound by theory, the % conversion of starting unsaturated fatty acid to the diacid product using our method was surprisingly superior to the prior art in that the dicarboxylic acids generated during the reaction were precipitated from the reaction mixture. In other words, as the self-metathesis of the starting unsaturated fatty acid proceeded the diacid product surprisingly precipitated out of the solution and the equilibrium was shifted to favor formation of the diacid product, which improved the conversion and hence isolated yield of diacid product.

Surprisingly, we were able to form the unsaturated-α,ω-dicarboxylic acids in one-step with very high conversion (e.g., >about 80%) and isolated yields (e.g., >about 70%) of dibasic acids. The process also surprisingly worked well with fatty acid mixtures such as those derived from oils (see Example 2 below). The reaction can be performed between temperatures ranging from about 50° C. to about 53° C.; this temperature range was critical since the starting cis unsaturated fatty acids isomerize rapidly to the trans isomers, whose melting points are higher than the starting cis isomers, and at reaction temperatures below 40° C. the reaction mixture solidifies which inhibits the metathesis reaction. On the other hand, at temperatures above 55° C. the reaction mixture remained liquid and the metathesis reaction was equilibrium controlled and hence the conversion to diacid products decreased. Surprisingly at the temperature ranging from about 50° C. to about 53° C. the starting fatty acids remained liquid and further reacted with the catalyst to generate more diacids whereas the diacids formed precipitated from the reaction mixture, which increased conversion of starting acid to diacid product.

Example 2

The results above led us to further explore the olefin metathesis process using less expensive feedstocks such as vegetable oil- and animal fat-derived fatty acids.

Soybean oil (refined, bleached, deodorized) was a gift from Archer Daniels Midland (ADM, Decatur, Ill.). Canola oil (rapeseed) was from Archer Daniels Midland Co., ADM (Decatur, Ill.). Tall oil fatty acid was from Arizona Chemical (Jacksonville, Fla.). Linseed oil and bis-(2,4,6-trimethylphenyl)-2-(imidazolidinylidene)(dichlorophenylmethylene)-(tricyclohexylphosphine) [RuCl$_2$(=CHPh)(H$_2$IMes)(PCy$_3$)] 2, a $2^{nd}$ generation Grubbs catalyst, used in this study were from Aldrich Chemical (Milwaukee, Wis.). All other reagents used were of the highest purity obtainable from commercial suppliers.

The vegetable oils were hydrolyzed to their free fatty acids (FFA) using 1 M KOH in ethanol:water (95:5) (Christie, W. W., Lipid analysis: Isolation, Separation, Identification, and Structural Analysis of Lipids, Oxford, N.Y., Pergamon Press, 1982). The fatty acid distributions in the FFA mixtures are listed in Table 3.

GC was carried out with a Hewlett Packard (Agilent, Wilmington, Del.) HP 6890 instrument equipped with an on-column capillary inlet (splitless mode) and an FID detector set at 370° C. The capillary column used was a Zebron ZB-5 column (30 m×0.25 mm×0.25 µm) with $N_2$ as carrier gas set at 1 mL/min constant flow. The oven temperature profile was as follows: initial temperature 50° C.; hold for 8 min.; ramp at 15° C./min to 220° C.; hold for 10 min.; ramp at 15° C./min. to 250° C.; hold for 15 min. GC/MS was carried out with a Hewlett Packard HP 5890 instrument with a capillary inlet (split-split mode) and an HP Model 5972 mass detector set to scan from 40 to 550 m/z at of 1.5 scans/s. The capillary column used was a HP DB-5 column (30 m×0.25 mm×0.25 µm) with carrier gas (He) set at a linear velocity of 22 cm/sec at 100° C. The injector and detector transfer line temperatures were set at 250° and 280° C., respectively. The oven temperature profile was as above for the GC analyses.

Figure 4:
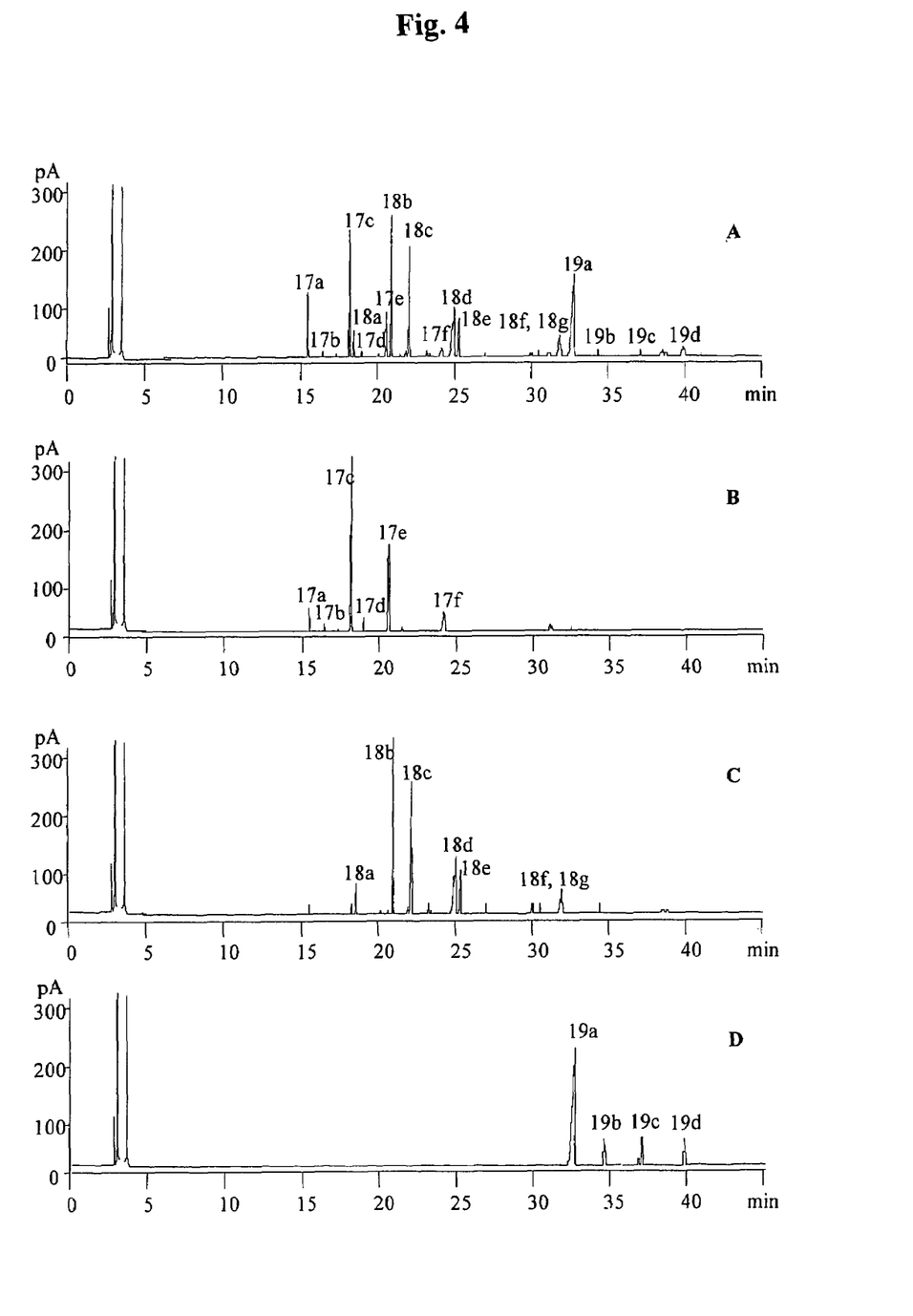
FIG. 4 shows GC chromatograms of total product obtained from the metathesis soy fatty acids (Panel A) and after fractionation by column chromatography; Panels (B) hydrocarbon fraction; (C) mono-fatty acid fraction; and (D) diacid fraction. Peak numbers correspond to structures shown in FIG. 5.
Figure 5:
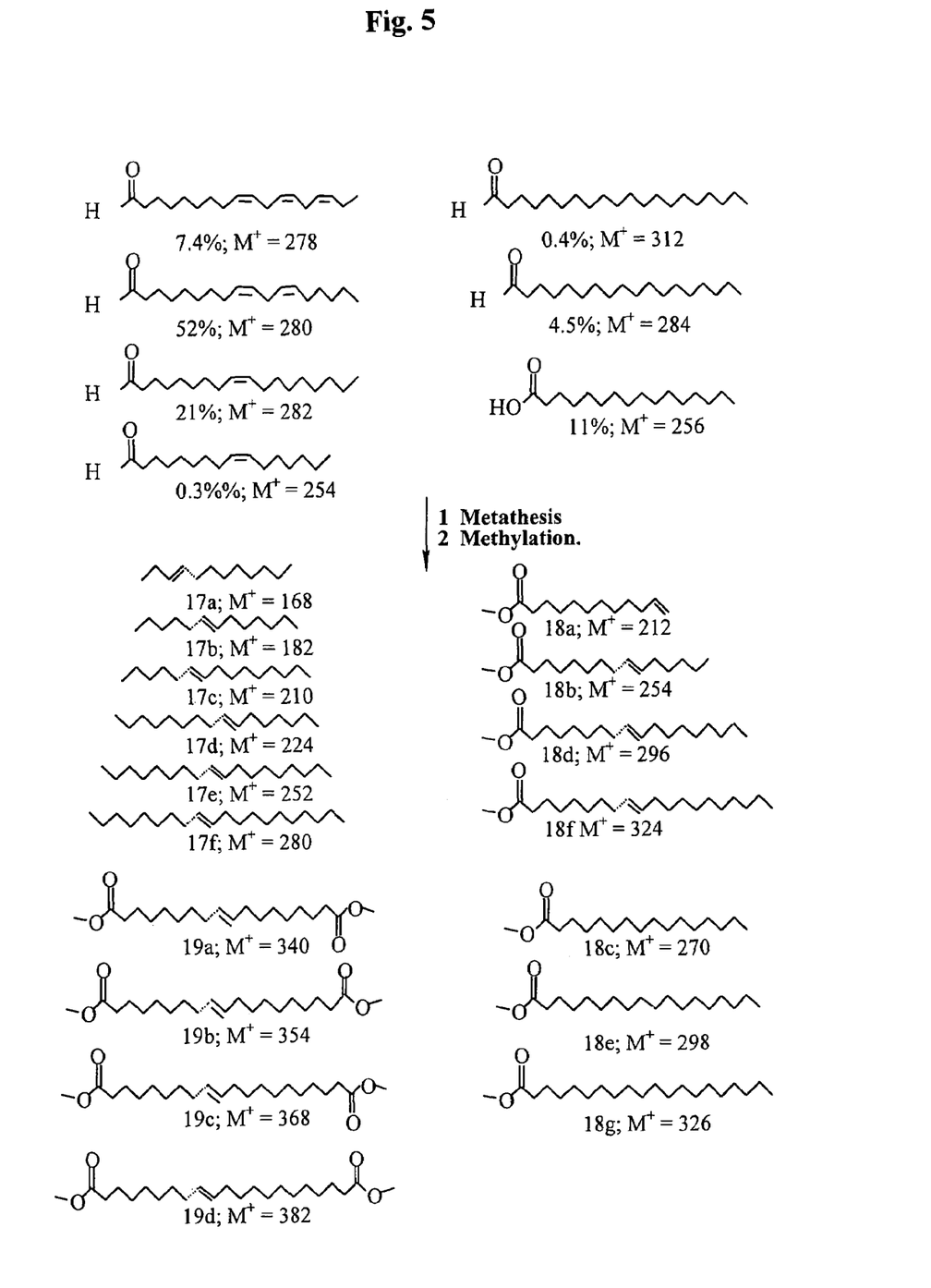
FIG. 5 shows products formed during the self-metathesis of soy fatty acids in the presence of 0.01 mol % of ruthenium catalyst 2.

Synthesis of diacids 19a-19d (FIG. 4) from soy fatty acids (SFA): SFA (16b (Table 3) 2.5 g, 8.9 mmol) and ruthenium catalyst 2 (7.5 mg, 0.9 mmol) were added to a 25 mL, 2-neck round bottom flask under a nitrogen flow. The reaction mixture was stirred and heated at 53° C. and after ~2 hours a precipitate formed. After a total of 8 h reaction, the reaction was quenched with ethyl vinyl ether (~3 mL) and the reaction mixture transferred to a 50 mL 1-neck flask. The solvent was removed under reduced pressure and the dried product residue methylated with methanol (35 mL) containing conc. sulfuric acid (10 drops). The resulting mixture was heated to reflux for 1 hour, cooled to room temperature, quenched with 50 mL of saturated $Na_2CO_3$, extracted with ethyl ether (2×75 mL) and the combined ether layers washed with water (3×50 mL). The organic layer was dried with $MgSO_4$, filtered, and the solvent removed under reduced pressure. The GC trace of the total methylated product is shown in FIG. 4A. The crude methylated product (1 g) was purified by silica gel chromatography column using hexane:ethyl acetate (95:5 v/v) as eluent to give 52 mg of a hydrocarbon fraction (17a-17f, FIG. 5) as a colorless liquid; 500 mg of mixed unsaturated and saturated fatty methyl esters (18a-18g, FIG. 5); and 427 mg of unsaturated dicarboxylate methyl esters (compounds 19a-19d, FIG. 5). GC chromatograms for the isolated fractions are shown in FIGS. 4B-D, respectively. The GC/MS spectrum of the methyl esters of 19a-19d showed [M]⁺ ions at m/z 340 (19a), m/z 354 (19b), m/z 368 (19c), and m/z 382 (19d). The proposed structures corresponding to these molecular [M]⁺ ions are shown in FIG. 5. The ¹H NMR spectrum of methylated diacids 19a-19d (CDCl₃, 200 MHz) had signals at: δ 5.37 (m, —CH═CH—, 2H), 3.66 (s, —CH₂CO₂CH₃, 6H), 2.3 (t, J=7.2 Hz & 7.8 Hz, —CH₂CO₂CH₃, 4H), 1.97 (m, 4H), 1.61 (m, 5H) 1.29 (s, 15H). ¹³C NMR (CDCl₃, 50 MHz): δ 174.2 (s, —CO₂CH₃), 130.4 (s, —CH═CH—), 51.4 (s, —CH₂CO₂CH₃), 34.2 (s), 32.6 (s), 29.7 (s), 29.2 (s), 29 (s), 25 (s). GC/MS analysis indicated that the diacids generated were predominately $C_{18}$ fatty acids.

The self-metathesis of SFA also was carried out as above on a 50 g scale in a 3-neck, 250 mL round bottom flask equipped with a mechanical stirrer. The crude acid product obtained was fractionally distilled at 0.5 mm Hg. From 35.5 g of crude acid product the following fractions were obtained: a hydrocarbon fraction (17a-17d, ~3 g) as a colorless oil over the temperature range of 110° to 120° C.; a monocarboxylic acid fraction (18a-18g, ~19 g) over the temperature range of 140° to 210° C., which solidified to a white solid (m. p.=36-38° C.); and a light brown solid residue composed primarily of diacids (19a-19d, ~14 g). The diacid fraction, which contained <10% mono-fatty acids (by GC), was purified by recrystallization from a mixture of ethyl acetate (~30 mL) and hexane (~100 mL) at 3° C. to give diacids 19a-19d as a light brown solid [m. p.=97.5-99.5° C.] in an isolated yield of 12 g (73%). ¹H NMR of diacids 19a-19d (CD₃OD, 200 MHz): δ 5.35 (m, —CH═CH—, 2H), 2.28 (t, J=7.2 Hz & 7.6 Hz, —CH₂CO₂H, 4H), 1.98 (m, 4H), 1.60 (m, 4H), 1.32 (m, 16H). ¹³C NMR (CD₃OD, 50 MHz): δ 177.8 (s, CO₂H), 131.7 (s, CH═CH), 35.1 (s), 33.8 (s), 30.9 (s), 30.4 (s), 30.2 (s), 26.2 (s). GC and GC/MS showed that the diacids were predominantly $C_{18}$ fatty acids.

Figure 6:
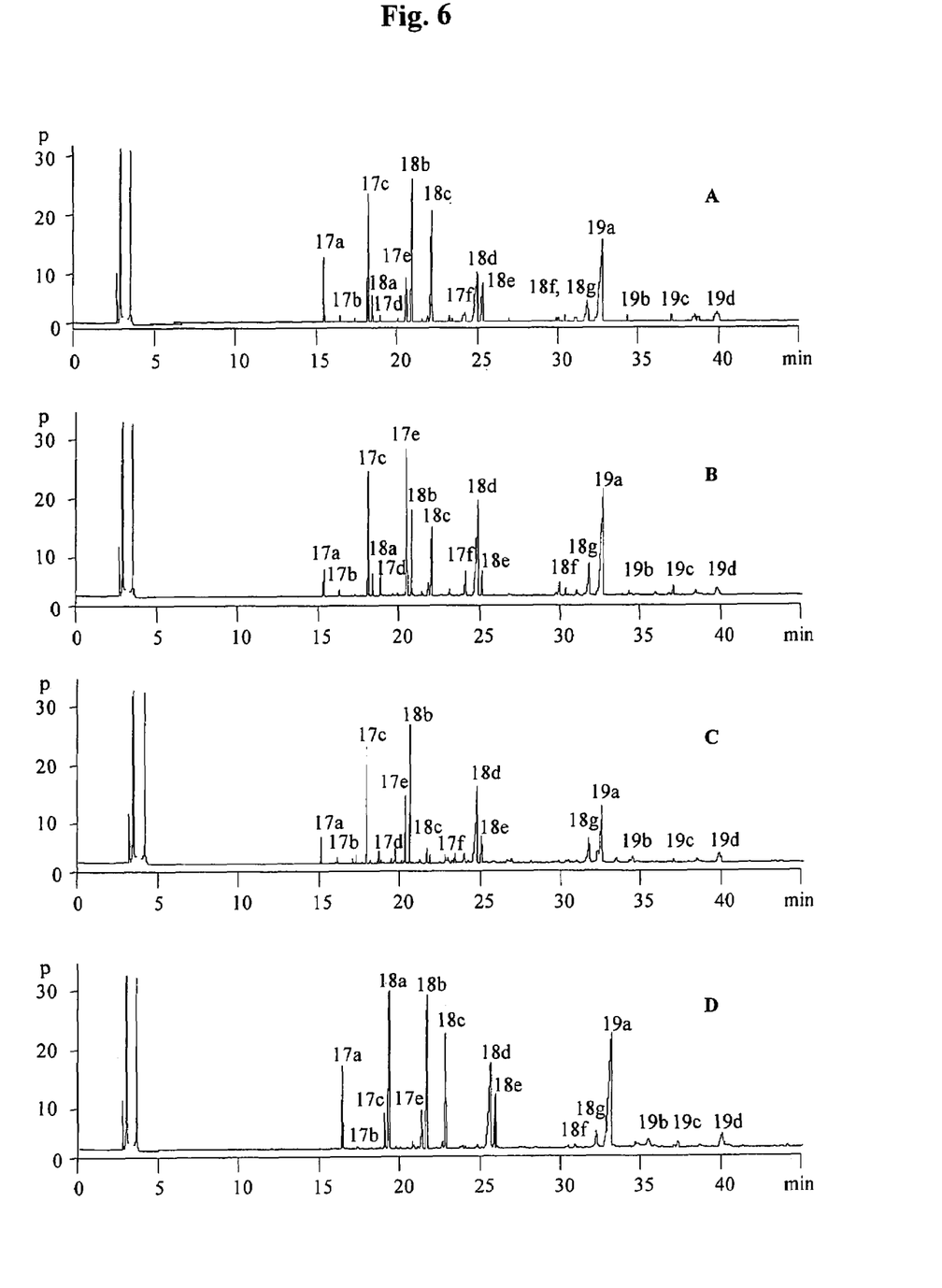
FIG. 6 shows GC traces of total products obtained from the metathesis of soy (A), rapeseed (B), tall (C), and linseed (D) fatty acids.

Synthesis of diacids (19a-19d) from rapeseed fatty acids (RFA): RFA ((16c, (Table 3) 2.5 g, 8.9 mmol) were metathesized with catalyst 2 (7.5 mg, 8.8 mmol) at 53° C. After ~2 h reaction a significant amount of precipitate was observed in the reaction mixture. After an additional 6 h reaction the acid mixture was isolated and methylated as described above. GC trace of the total methylated product is shown in FIG. 6B. The crude product (1 g) was purified by silica gel column to give 188 mg of a hydrocarbon mixture (17a-17f, FIG. 4), 420 mg of unsaturated fatty methyl esters (18a-18g, FIG. 4), and 390 mg of unsaturated dicarboxylate methyl esters (19a-19d, FIG. 4). GC/MS of the methyl esters of diacids 19a-19d gave [M]⁺ ions at m/z 340 (19a), m/z 354 (19b), m/z 368 (19c), m/z 382 (19d). ¹H NMR of methylated diacids 19a-19d (CDCl₃, 200 MHz): δ 5.37 (m, —CH═CH—, 2H), 3.66 (s, —CH₂CO₂CH₃, 6H), 2.3 (t, J=7.2 Hz & 7.8 Hz, —CH₂CO₂CH₃, 4H), 1.97 (m, 4H), 1.61 (m, 5H) 1.29 (s, 15H). ¹³C NMR (CDCl₃, 50 MHz): δ 174.4 (s, —CO₂CH₃), 130.5 (s, —CH═CH—), 51.6 (s, —CH₂CO₂CH₃), 34.3 (s), 32.7 (s), 29.7 (s), 29.3 (s), 29.1 (s), 25.1 (s). GC and GC/MS showed that the diacids were predominantly $C_{18}$ chain-length and that 19a predominated (FIG. 6B).

In larger scale reactions, the crude acid product mixtures were purified by vacuum distillation at 0.5 mm Hg. From 99.7 g of crude metathesized rapeseed acids the following fractions were obtained: a hydrocarbon fraction (17a-17d, ~17 g) over the temperature range of 1100-160° C.; a mono-fatty acid fraction, (18a-18e, ~44 g) over a temperature range of 170°-210° C.; and a solid residue composed primarily of diacids (19a-19d, ~41 g). The diacid residue was recrystallized from a mixture of hexane (100 mL) and ethyl acetate (10 mL) at –3° C. to give ~40 g (78% yield) of diacids 19a-19d as a yellow solid [m.p.=96.5-98.5° C.]. ¹H NMR of acid form of 19a-19d (CD₃OD, 200 MHz): δ 5.4 (m, —CH═CH—, 2H), 2.25 (t, J=7.6 Hz & 7.2 Hz, —CH₂CO₂H, 4H), 1.95 (m, 4H), 1.6 (m, 4H), 1.3 (m, 16H). ¹³C NMR (CD₃OD, 50 MHz): δ 177.9 (s, CO₂H), 131.7 (s, CH═CH), 35.1 (s, CH₂CO₂H), 33.7 (s), 30.8 (s), 30.4 (s), 30.2 (s), 26.2 (s).

Synthesis of diacids (19a-19d) from tall acids (TFA): TFA (16d, (Table 3) 2.5 g, 8.9 mmol) and were metathesized with catalyst 2 (7.5 mg, 8.8 mmol) under conditions used for SFA. At the end of the reaction (12 h) only a small amount of diacid precipitate was observed. The crude reaction mixture was isolated and methylated as above. The GC chromatogram for this methyl ester product is shown in FIG. 6C. The crude ester product (1 g) was fractionally separated by silica gel chromatography using hexane:ethyl acetate (95:5 v/v) as the eluant into a hydrocarbon fraction (17a-17c, 126 mg); an unsaturated fatty methyl ester fraction (18a-18g, 460 mg); and a dimethyl ester fraction (19a-19d, 380 mg, 70% yield). The diester fraction (19a-19d) was analyzed by GC/MS: (retention time=27.5-34 min FIG. 5c) and showed [M]+ ions of m/z 340 (19a); m/z 354 (19b); m/z 368 (19c); and m/z 382 (19d).

Synthesis of diacids (19a-19d) from linseed acids (LFA): LFA (16e (Table 3), 2.5 mg, 8.9 mmol) were metathesized with catalyst 2 (7.5 mg, 8.8 mmol) as described for SFA. Only a small amount of diacid precipitate was observed after ~12 h reaction. The reaction was worked up and methylated as above. The GC chromatogram for this methyl ester product is shown in FIG. 6D. 1 g of the crude methylated product was separated into hydrocarbon, mono fatty acid ester, and di-fatty acid ester fractions by silica chromatography. The diester fraction was analyzed by GC/MS and gave [M]+ ions for dimethyl esters of 19a-19d at: m/z 340 (19a); m/z 354 (19b); m/z 368 (19c); m/z 382 (19d); with diester 19a predominating.

Results and Discussion: Long-chain oils such as soy, rapeseed, tall, and linseed, which contain a high proportion of $C_{18}$ chain-length unsaturated fatty acids, were subjected to olefin metathesis using Grubbs' catalyst 2. The oils were first hydrolyzed under basic condition to their corresponding free fatty acids. The compositions of the fatty acid mixtures obtained from the oils after hydrolysis are listed in Table 3. Hydrolysis of soy oil gave a mixture of fatty acids (16b, Table 3) with the following composition: (21%) oleic acid with one double bond; (52%) linoleic acid with two double bonds; and (7.4%) linolenic acid with three double bonds (Table 4, entry 2). The unsaturated fatty acids derived from rapeseed, tall, and linseed oils also are listed in Table 3 and their fatty acid distributions correspond to those reported previously (Christie, W. W., Lipid analysis: Isolation, Separation, Identification, and Structural Analysis of Lipids, Oxford, N.Y., Pergamon Press, 1982). In contrast to previous studies, the metathesis reactions in this study were carried out in the presence of catalyst 2 under solvent-free conditions. Extensive self- and cross-metathesis of the unsaturated FFA mixtures surprisingly afforded two additional product classes, namely unsaturated hydrocarbons and unsaturated dicarboxylic acids in high molar conversions. When SFA (16b, Table 3) were metathesized using a 0.1 mol % catalyst loading, at a reaction temperature between 50°-53° C., newly formed diacid products surprisingly started to precipitate from the reaction milieu in ~2 h. After a total reaction time of 8 h, the reaction was terminated, the crude product isolated, and the acid products converted to methyl esters. As shown in FIG. 4A, the ester product obtained was a complex mixture since the oleic, linoleic, and linolenic acids in the SFA mixture undergo both self- and cross-metathesis type reactions. GC analysis of this product, however, surprisingly indicated an 88% conversion of the starting unsaturated fatty acids to metathesis products and similar conversions were obtained in larger scale reactions. The mixtures could be separated into a hydrocarbon, mono-ester, and di-ester fractions by silica gel column chromatography as shown in FIGS. 4B-D, respectively. A similar separation was made in larger scale reactions by fractional distillation of the crude acid product that surprisingly gave an 88% isolated yield of diacid product. The isolated hydrocarbon and mono- and di-ester or acid fractions were subsequently characterized by GC/MS and $^1$H and $^{13}$C NMR spectroscopy. FIG. 5 shows the starting fatty methyl esters in SFA and the methylated metathesis products that were identified. The saturated fatty acids hexadecanoic (18c), octadecanoic (18e), and eicosanoic (18g), which are saturated fatty acids, did not undergo metathesis and remained in the product mixture. Dodecene (17a), pentadecene (17c), pentadecenoic (17b), and 1,18-octadecenedioic (19a) were the major metathesis products identified (FIG. 4). Tridecene (17b), dodecenoic (18a), hexadecene (17d), eicodecene (17f), and 1,19-nonadecenedioic (19b), 1,20-eicosecenedioic (19c), and 1,21-heneicosendioic (19d) acid were present as minor products (FIG. 5). Without being bound by theory, the latter products were thought to result from secondary metathesis reactions of the initially formed alkenes and unsaturated acids. Octadecenoic (18d) and eicosenoic (18f) acid, present in the starting SFA, also were minor components of the reaction product. It should be noted that all of the unsaturated mono- and diacids products obtained were predominately trans isomers. The yield of diacid products did not improve beyond 8 h reaction nor did the conversion of SFA and no change in product distribution occur with longer reaction times or conditions (Table 4, entries 1-3). The metathesis reactions surprisingly also worked well at 0.01 mol % catalyst loading giving an 86% conversion of starting fatty acids to products and a 75% isolated yield of diacids (Table 4, entry 4).

We also carried out control experiments using soy methyl esters under similar reaction conditions. When ester mixture 16a was treated with 0.01 mol % catalyst 2, surprisingly an equilibrium distribution of products (51% molar conversion) and a diester fraction was obtained in an isolated yield of 50% (Table 4, entries 5, 6). In general, a decrease in both SFA conversion and yield of diester fraction was obtained in the metathesis of fatty acid methyl esters compared to the acid mixtures. This was a result of the greater miscibility of the metathesis products in ester reactions compared to the free acid reactions. A higher catalyst loading (0.1 mol %) of 2 gave an 89% conversion of starting esters but only a 60% isolated yield of diesters (19a-19d) (Table 4, entry 7). Again, the soy acids gave higher yields because of the lower solubility of diacids in the soy acid mixtures. As olefin metathesis of SFA proceeded, the long-chain diacids precipitated out of the solution and the equilibrium was shifted to the diacid products. Thus, it was worth noting that it was critical to run the metathesis reactions in the temperature range of 45°-55° C. If the temperature was below 40° C. the reaction mixture solidified which resulted in a lower conversion of starting fatty acids. In contrast, if the temperature was above 55° C. the reaction mixture remained liquid and lower yields of diacids were obtained since they underwent further cross metathesis. With the reaction conditions used in this work, the precipitation of the diacid mixtures surprisingly increased both the conversion of starting unsaturated fatty acids and yields of the diacid products.

Fatty acid mixtures derived from rapeseed, tall, and linseed oils also were prepared using the solvent-free olefin metathesis conditions reported herein. Relatively high conversions and isolated yields of diacid mixtures were surprisingly obtained when the molar ratio of fatty acids to catalyst 2 was 1000:1 (Table 4, entries 8-15). This suggested that the ratio of oleic, linoleic, and linolenic surprisingly had little affect on either the conversion or yield of diacid product obtained in this study. The product distribution obtained for these acid mixtures varied but in general was similar to the product mixture obtained with the soy fatty acids (FIG. 6). When the molar ratio of fatty acids to catalyst 2 was 10,000:1, these acid mixtures did not metathesize as well as the soy acid mixture in that the conversion of starting acids and diacid yields dropped significantly. Of the fatty acid mixtures examined in this study (Table 4), the soy fatty acid mixture surprisingly gave the best results for olefin metathesis of unsaturated fatty acids to diacid products even at low catalyst loadings. For example, in the presence of 0.005 mol % catalyst, the metathesis of soy acids at 75° C. for 20 h surprisingly gave a 63% conversion and an isolated yield (50%) of diacids (Table 4, entry 4).

Overall the process reported represents an efficient route to the synthesis of long chain symmetrically unsaturated-α,ω-dicarboxylic acids. This solvent-free metathesis process worked well with unsaturated mixtures of fatty acids derived from a variety of oils. High conversions to products were obtained for the fatty acids from soy, rapeseed, tall, and linseed oils when the reactions were performed under solvent-free conditions and high yields of diacid products were obtained from these processes.

All of the references cited herein are incorporated by reference in their entirety. Also incorporated by reference in their entirety are the following U.S. Pat. Nos. 6,806,325; 6,515,084; 6,639,116; 6,211,391; 6,111,121 (especially the first, second and third formulas in column 5); 5,969,170; 5,922,863; 5,880,231; 5,849,851; 5,831,108; 5,750,815; 5,728,917; 5,710,298; 5,342,909; 5,312,940. Also incorporated by reference in their entirety are the following: Fuerstner, A., et al., Chem. Eur. J., 7: 3236-3253 (2001); Grubbs, R. H., et al., Tetrahedron, 54: 4413-4450 (1998); Holser, R. A., et al., Fuel, 85: 393-395 (2006); Ngo, H. L., and W. Lin, Top. Catal., 34: 85-92 (2005); Ngo, H. L., et al., J. Am. Oil. Chem. Soc., 83:629-634 (2006); Parshall, G. W., and S. D. Ittel, Homogeneous Catalysis, John Wiley & Sons, New York, 1992; Scholl, M. et al., Org. Lett., 1: 953-956 (1999); http://nobelprize.org/chemistry/laureates/2005/info.pdf.

Thus, in view of the above, the present invention concerns (in part) the following:

A method of producing dicarboxylic acids, said method comprising (or consisting essentially of or consisting of) reacting a compound having a terminal COOH and containing at least one carbon-carbon double bond with a second generation Grubbs catalyst in the absence of (added) solvent to produce dicarboxylic acids; wherein said method is conducted in an inert atmosphere.

The above method, wherein said catalyst is a ruthenium-based second generation Grubbs catalyst.

The above method, wherein said catalyst is selected from the group consisting of 1,3-bis-(2,4,6-trimethylphenyl)-2-(imidazolidinylidene)(dichlorophenylmethylene)-(tricyclohexylphosphine)ruthenium, or (1,3-Bis-(2,4,6-trimethylphenyl)-2-imidazolidinylidene)dichloro(o-isopropoxyphenylmethylene)ruthenium (or mixtures thereof).

The above method, wherein said inert atmosphere is nitrogen, argon, or nitrogen and argon. The above method, wherein said method is conducted in a nitrogen atmosphere.

The above method, wherein said compound is a carboxylic acid that contains one or more carbon-carbon double bonds located at the terminal or internal positions of the carboxylic acid chain. The above method, wherein said carboxylic acid has a chain-length of C-30 or less.

The above method, wherein said compound is a monounsaturated fatty acid having a chain length of from C-6 to C-30. The above method, wherein said fatty acid is a monounsaturated fatty acid containing an internal carbon-carbon double bond with either a cis (Z) or trans (E) configuration. The above method, wherein said fatty acid is selected from the group consisting of lauroleic acid, myristoleic acid, palmitioleic acid, oleic acid, elaidic acid, gadoleic acid, erucic acid, 11-eicosenoic acid, and mixtures thereof.

The above method, wherein said compound is a polyunsaturated fatty acid having a chain length of from C-12 to C-30 and having 2 to 6 internal carbon-carbon double bonds. The above method, wherein said fatty acid is selected from the group consisting of linoleic acid, linolenic acid, arachadonic acid, docosadienoic acid, eicosatrienoic acid, arachadonic acid, eicosatetraenoic acid, docosatetraenoic acid, decosapentaenoic acid, eicosapentaenoic acid, docosahexaenoic acid, tetracosahexaenoic acid, and mixtures thereof. The above method, wherein said fatty acid contains at least one branched chain containing from C-1 to C-20.

The above method, wherein said compound is a terminally monounsaturated fatty acid having a chain length of from C-6 to C-30. The above method, wherein said fatty acid is selected from the group consisting of 10-undecenoic acid or 9-deceneoic acid (or mixtures thereof).

The above method, wherein said compounds are selected from the group consisting of oleic acid, 11-eicosenoic acid, erucic acid, undecenoic acid, ricinoleic acid, linoleic acid, or ricinoleic acid (or mixtures thereof). The above method, wherein said compound is selected from the group consisting of oleic acid, erucic acid, or ricinoleic acid (or mixtures thereof).

The above method, wherein said dicarboxylic acids are selected from the group consisting of 1,18-octadec-9-enedioic acid, 1,22-docos-11-enedioic acid, 1,26-hexacos-13-enedioic acid, 1,20-eicos-1,0-enedioic acid, or 7,12-dihydroxyoctadec-9-ene (or mixtures thereof).

The above method, wherein said dicarboxylic acids are α,ω-unsaturated dicarboxylic acids.

The above method, wherein said compound is from acids obtained from oilseeds.

The method according to claim 1, wherein said method is conducted at a temperature of about 20° to about 100° C. or about 40° to about 60° C. or about 40° to about 55° C. or about 45° to about 55° C. or about 45° to about 50° C. or about 45° to about 49° C. (e.g., 45° to 49° C.) or about 45° to about 48° C. (e.g., 45° to 48° C.) or about 45° to about 47° C. (e.g., 45° to 47° C.) or about 45° to about 46° C. (e.g., 45° to 46° C.) or about 45° C. or any range of temperatures between about 40° to about 55° C. (e.g., any range of temperatures between 40° to 55° C.).

The above method, wherein said dicarboxylic acids precipitate and are removed (e.g., by filtration or other methods known in the art).

The above method, further comprising reacting said dicarboxylic acids with an alcohol (e.g., lower alkyl) to produce esters thereof. Wherein said alcohol is selected from the group consisting of methanol, ethanol, and mixtures thereof.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Ruthenium-Catalyzed Self-Metathesis of Unsaturated Fatty Acids/Esters[a]

| Entry | Fatty Ester/Acid[b] | % conv.[c] | % Isolated Diester/ Acid | α,ω-Dicarboxylic Ester/Acid | Alkene |
|---|---|---|---|---|---|
| 1 | Methyl Oleate (3a, 99%) | 50 | 39[d] | 1,18-Dimethyl Octadec-9-enedioate (5a) | Octadec-9-ene |
| 2 | Oleic Acid (3b, 90%) | 79 | 71[e] | 1,18-Octadec-9-enedioic Acid (5b) | Octadec-9-ene (4) |

TABLE 1-continued

Ruthenium-Catalyzed Self-Metathesis of Unsaturated Fatty Acids/Esters[a]

| Entry | Fatty Ester/Acid[b] | % conv.[c] | % Isolated Diester/Acid | α,ω-Dicarboxylic Ester/Acid | Alkene |
|---|---|---|---|---|---|
| 3 | 11-Eicosenoic Acid (3c, 99%) | 77 | 74[e] | 1,22-Docos-11-enedioic Acid (5c) | Octadec-9-ene |
| 4 | Erucic Acid (3d, 90%) | 74 | 70[f] | 1,26-Hexacos-13-enedioic Acid (5d) | Octadec-9-ene |
| 5 | Undecenoic Acid (6, 98%) | 87 | 82[e] | 1,20-Eicos-10-enedioic Acid (7) | Ethene |
| 6 | Ricinoleic Acid (8, 99%) | 63 | 40[f,g,h] | 1,18-Octadec-9-enedioic Acid (5b) | 7,12-Dihydroxy-octadec-9-ene (9) |
| 7 | Linoleic Acid (10, 99%) | 56 | — | Mixture of Diacids[h] | Mixture of alkenes[i] |

[a]All the reactions were carried out with 0.1 mol % catalyst 2 (FIG. 1) at 45° C. for 3 days.
[b]Starting fatty acid/ester (percent purity) and products shown in FIGS. 2 and 3.
[c]Determined by GC and expressed as (Σ alkene + diacid)/(Σ alkene + diacid + fatty acid). Dodecane used as the internal reference.
[d]Dimethyl ester isolated by silica gel chromatography.
[e]Isolated by recrystallizing from hexane/ethyl acetate.
[f]Isolated by recrystallizing from acetone.
[g]Product was methyl octadec-9-enedioate.
[h]Reaction carried out at 1.0 mol % catalyst loading.
[h]Diacid product (35%) composed of the following acids: C18:1; C21:5; C26:3 as determined by GC/MS of the reaction product after conversion to methyl esters.
[i]Alkene product (24%) composed of the following alkenes: C12:1; C15:2; C18:3 as determined by GC/MS of reaction mixture.

TABLE 2

Effect of Catalyst Loading on the Ruthenium-Catalyzed Metathesis of Unsaturated Fatty Acids[a]

| Entry | Fatty acids | Catalyst loading (mol %) | % Conversion[b] | TON[c] |
|---|---|---|---|---|
| 1 | Oleic (3b, 90%) | 0.1 | 79 | 790 |
| 2 | Oleic (3b, 90%) | 0.01 | 66 | 6600 |
| 3 | Oleic (3b, 90%) | 0.005 | 54 | 10,800 |
| 4 | Undecenoic (6, 98%) | 0.1 | 87 | 870 |
| 5 | Undecenoic (6, 98%) | 0.01 | 64 | 6400 |

[a]All reactions were carried out with catalyst 2 (FIG. 1) at 45° C. for 48 h.
[b]Determined by GC and expressed as (Σ alkene + diacid)/(Σ alkene + diacid + fatty acid).
[c]TON = catalyst turnover number defined as % conversion/mol % catalyst loading.
[d]Acid dried with molecular sieves for 24 h and then vacuum distilled at 180° C. before use.

TABLE 3

% Composition of Fatty Acids Derived from Hydrolysis of Fats and Oils

| Fatty acid/ester (% wt %) | C16:0 | C16:1 | C18:0 | C18:1 | C18:2 | C18:3 | C20:0 | Unidentified |
|---|---|---|---|---|---|---|---|---|
| Soy methyl esters (16a) | 11 | 0.3 | 4.5 | 21 | 52 | 7.4 | 0.4 | 3.4 |
| Soy acids (16b) | 11 | 0.3 | 4.5 | 21 | 52 | 7.4 | 0.4 | 3.4 |
| Rapeseed acids (16c) | 3.8 | 0.2 | 1.9 | 57 | 21 | 10 | 0.6 | 5.5 |
| Tall acids (16d) | 0.8 | 0.9 | 3.4 | 55 | 24 | 0 | 1.8 | 14 |
| Linseed acids (16e) | 5.6 | 0 | 3.8 | 20 | 18 | 51 | 0 | 1.4 |

[a]GC was carried out with a Hewlett Packard HP 5890 instrument with a capillary inlet (split-split mode). The capillary column used was a SP™ 2340 column (30 m × 0.25 mm 0.2 μm) with carrier gas (He) set at a linear velocity of 22 cm/sec at 180° C. The injector and detector transfer line temperatures were set at 220 and 250° C., respectively. The oven temperature profile was: initial temperature 180° C.; hold for 10 min.; ramp at 2° C./min to 190° C.; hold for 10 min.

TABLE 4

Olefin Metathesis of Unsaturated Fatty Acids with 2nd Generation Grubbs Catalyst

| Entry | Fatty acid/ester | C16:0 + C18:0 + C20:0[i] | C18:1 + C18:2 + C18:3 + unknown[j] | % conv.[k] | Wt. % diacids[l] |
|---|---|---|---|---|---|
| 1 | Soy acids (16b)[a] | 16 | 84 | — | — |
| 2 | Soy acids (16b)[b,c] | 16 | 10 | 88 | 88 |
| 3 | Soy acids (16b)[b,e] | 17 | 9.9 | 88 | 88, 73[m] |
| 4 | Soy acids (16b)[b,f] | 16 | 12 | 86 | 75 |
| 5 | Soy methyl esters (16a)[a] | 16 | 84 | — | — |
| 6 | Soy methyl esters (16a)[b,f] | 16 | 41 | 51 | 50 |
| 7 | Soy methyl esters (16a)[b,e] | 16 | 9.6 | 89 | 60 |
| 8 | Rapeseed acids (16c)[a] | 6.3 | 94 | — | — |
| 9 | Rapeseed acids (16c)[b,c] | 6.9 | 19 | 80 | 72 |
| 10 | Rapeseed acids (16c)[b,f] | 6.9 | 41 | 56 | 48 |
| 11 | Tall acids (16d)[a] | 6.0 | 94 | — | — |
| 12 | Tall acids (16d)[b,d] | 6.0 | 17 | 82 | 70 |
| 13 | Tall acids (16d)[b,g,h] | 6.0 | 53 | 43 | — |

TABLE 4-continued

Olefin Metathesis of Unsaturated Fatty Acids
with 2$^{nd}$ Generation Grubbs Catalyst

| | | % Fatty acid composition from gas chromatography | | | |
|---|---|---|---|---|---|
| Entry | Fatty acid/ester | C16:0 + C18:0 + C20:0$^i$ | C18:1 + C18:2 + C18:3 + unknown$^j$ | % conv.$^k$ | Wt. % diacids$^l$ |
| 14 | Linseed acids (16e)$^a$ | 9.9 | 90 | — | — |
| 15 | Linseed acids (16e)$^{b,d}$ | 9.9 | 13 | 86 | 79 |

$^a$Composition of fatty acids before reaction.
$^b$Composition of fatty acids after reaction.
$^c$Reaction was run with 0.1 mol % catalyst 2 loading at 53° C. for 8 h.
$^d$Reaction was run with 0.1 mol % catalyst 2 loading at 53° C. for 20 h.
$^e$Reaction was run with 0.1 mol % catalyst 2 loading at 53° C. for 3 days.
$^f$Reaction was run with 0.01 mol % catalyst 2 loading at 50° C. for 20 h.
$^g$Reaction was run with 0.01 mol % catalyst 2 loading at 50° C. for 3 days.
$^h$Did not observe any precipitation.
$^i$Composition of SFA summed.
$^j$Composition of UFA + unknown summed.
Unknown was added to the total because the unknown peaks disappeared after reaction.
$^k$% conversion = [(Σinitial UFA − Σfinal UFA)/(Σinitial UFA)].
$^l$Isolated yields of diacid mixtures after methylation and purification with silica gel chromatography column with hexane:ethyl acetate (95:5 v/v) as an eluent.
$^m$Isolated yields of diacid mixtures by vacuum distillation at high temperature.

We claim:

1. A method of producing dicarboxylic acids, said method comprising reacting at a temperature of about 45° to about 55° C. a compound having a terminal COOH and containing at least one carbon-carbon double bond with a second generation Grubbs catalyst in the absence of solvent to produce dicarboxylic acids wherein said dicarboxylic acids precipitate and are removed; wherein said method is conducted in an inert atmosphere; wherein the yield of said dicarboxylic acids is about 70% to about 90%.

2. The method according to claim 1, wherein said catalyst is a ruthenium-based second generation Grubbs catalyst.

3. The method according to claim 1, wherein said catalyst is selected from the group consisting of 1,3-bis-(2,4,6-trimethylphenyl)-2-(imidazolidinylidene)(dichlorophenylmethylene)(tricyclohexylphosphine)ruthenium, (1,3-Bis-(2,4,6-trimethylphenyl)-2-imidazolidinylidene)dichloro(o-isopropoxyphenylmethylene)ruthenium, and mixtures thereof.

4. The method according to claim 1, wherein said inert atmosphere is nitrogen, argon, or nitrogen and argon.

5. The method according to claim 1, wherein said method is conducted in a nitrogen atmosphere.

6. The method according to claim 1, wherein said compound has a chain-length of C-30 or less.

7. The method according to claim 1, wherein said compound is a monounsaturated fatty acid containing an internal carbon-carbon double bond with either a cis (Z) or trans (E) configuration and having a chain length of from C-6 to C-30.

8. The method according to claim 7, wherein said compound is selected from the group consisting of lauroleic acid, myristoleic acid, palmitioleic acid, oleic acid, elaidic acid, gadoleic acid, erucic acid, 11-eicosenoic acid, and mixtures thereof.

9. The method according to claim 1, wherein said compound is a polyunsaturated fatty acid having a chain length of from C-12 to C-30 and having 2 to 6 internal carbon-carbon double bonds.

10. The method according to claim 9, wherein said compound is selected from the group consisting of linoleic acid, linolenic acid, arachadonic acid, docosadienoic acid, eicosatrienoic acid, arachadonic acid, eicosatetraenoic acid, docosatetraenoic acid, decosapentaenoic acid, eicosapentaenoic acid, docosahexaenoic acid, tetracosahexaenoic acid, and mixtures thereof.

11. The method according to claim 1, wherein said compound is a terminally monounsaturated fatty acid having a chain length of from C-6 to C-30.

12. The method according to claim 11, wherein said compound is selected from the group consisting of 10-undecenoic acid, 9-deceneoic acid, and mixtures thereof.

13. The method according to claim 1, wherein said compound is selected from the group consisting of oleic acid, 11-eicosenoic acid, erucic acid, undecenoic acid, ricinoleic acid, linoleic acid, ricinoleic acid, and mixtures thereof.

14. The method according to claim 1, wherein said compound is selected from the group consisting of oleic acid, erucic acid, ricinoleic acid, and mixtures thereof.

15. The method according to claim 1, wherein said dicarboxylic acids are selected from the group consisting of 1,18-octadec-9-enedioic acid, 1,22-docos-11-enedioic acid, 1,26-hexacos-13-enedioic acid, 1,20-eicos-10-enedioic acid, 7,12-dihydroxyoctadec-9-ene, and mixtures thereof.

16. The method according to claim 1, wherein said dicarboxylic acids are α,ω-unsaturated dicarboxylic acids.

17. The method according to claim 1, wherein said compound is obtained from oilseeds.

18. The method according to claim 1, wherein said dicarboxylic acids precipitate and are removed by filtration.

19. The method according to claim 1, further comprising reacting said dicarboxylic acids with an alcohol to produce esters thereof.

20. The method according to claim 19, wherein said alcohol is selected from the group consisting of methanol, ethanol, and mixtures thereof.

21. The method according to claim 1, wherein said temperature is 45° to 55° C.

22. The method according to claim 1, wherein said temperature is about 50° C. to about 53° C.

23. The method according to claim 1, wherein said yield is 70% to 90%.

24. The method according to claim 1, wherein said yield is about 75% to about 90%.

25. The method according to claim 1, wherein said yield is 75% to 90%.

26. The method according to claim 1, wherein the catalyst loadings of said second generation Grubbs catalyst is from about 0.001 mol % to about 0.1 mol % of reactants.

27. The method according to claim 1, wherein the catalyst loadings of said second generation Grubbs catalyst is from 0.001 mol % to 0.1 mol % of reactants.

28. The method according to claim 1, wherein the molar conversions of said compound having a terminal COOH and containing at least one carbon-carbon double bond to said dicarboxylic acids is about 70% to about 90%.

29. The method according to claim 1, wherein the molar conversions of said compound having a terminal COOH and containing at least one carbon-carbon double bond to said dicarboxylic acids is 70% to 90%.

30. The method according to claim 1, wherein the molar conversions of said compound having a terminal COOH and containing at least one carbon-carbon double bond to said dicarboxylic acids is about 75% to about 90%.

31. The method according to claim 1, wherein the molar conversions of said compound having a terminal COOH and containing at least one carbon-carbon double bond to said dicarboxylic acids is 75% to 90%.

32. The method according to claim 1, wherein said method consists essentially of reacting at a temperature of about 45° to about 55° C. a compound having a terminal COOH and containing at least one carbon-carbon double bond with a second generation Grubbs catalyst in the absence of solvent to produce dicarboxylic acids wherein said dicarboxylic acids precipitate and are removed, and optionally reacting said dicarboxylic acids with an alcohol to produce esters thereof; wherein said method is conducted in an inert atmosphere; wherein the yield of said dicarboxylic acids is about 70% to about 90%.

33. The method according to claim 1, wherein said method consists of reacting at a temperature of about 45° to about 55° C. a compound having a terminal COOH and containing at least one carbon-carbon double bond with a second generation Grubbs catalyst in the absence of solvent to produce dicarboxylic acids wherein said dicarboxylic acids precipitate and are removed, and optionally reacting said dicarboxylic acids with an alcohol to produce esters thereof; wherein said method is conducted in an inert atmosphere; wherein the yield of said dicarboxylic acids is about 70% to about 90%.

\* \* \* \* \*